(12) United States Patent
Slivka et al.

(10) Patent No.: US 7,066,938 B2
(45) Date of Patent: Jun. 27, 2006

(54) SNAP-ON SPINAL ROD CONNECTOR

(75) Inventors: Michael Andrew Slivka, Taunton, MA (US); William Lansing Dunbar, Norton, MA (US); Hassan Serhan, S. Easton, MA (US)

(73) Assignee: DePuy Spine, Inc., Raynham, MA (US)

( * ) Notice: Subject to any disclaimer, the term of this patent is extended or adjusted under 35 U.S.C. 154(b) by 604 days.

(21) Appl. No.: 10/237,508

(22) Filed: Sep. 9, 2002

(65) Prior Publication Data

US 2004/0049188 A1   Mar. 11, 2004

(51) Int. Cl.
*A61B 17/58* (2006.01)
(52) U.S. Cl. .......................................... 606/61
(58) Field of Classification Search ............. 606/61, 606/72
See application file for complete search history.

(56) References Cited

U.S. PATENT DOCUMENTS

| | | |
|---|---|---|
| 180,881 A | 8/1876 | Howson |
| 457,964 A | 8/1891 | Bolte |
| 483,342 A | 9/1892 | Bolte |
| 596,729 A | 1/1898 | White |
| 900,717 A | 10/1908 | Feaster |
| 1,455,441 A | 5/1923 | La Hodny |
| 2,638,301 A | 5/1953 | Smith |
| 3,019,504 A | 2/1962 | Castagliuolo |
| 3,499,222 A | 3/1970 | Linkow et al. |
| 3,752,203 A | 8/1973 | Hill, Jr. |
| 4,011,602 A | 3/1977 | Rybicki et al. |
| 4,085,744 A | 4/1978 | Lewis et al. |
| 4,179,905 A | 12/1979 | Schultenkamper |
| 4,289,124 A | 9/1981 | Zickel |
| 4,404,967 A | 9/1983 | Bacal et al. |
| 4,411,259 A | 10/1983 | Drummond |
| 4,611,580 A | 9/1986 | Wu |
| 4,611,581 A | 9/1986 | Steffee |
| 4,611,582 A | 9/1986 | Duff |
| 4,641,636 A | 2/1987 | Cotrel |
| 4,648,388 A | 3/1987 | Steffee |
| 4,653,481 A | 3/1987 | Howland et al. |
| 4,655,199 A | 4/1987 | Steffee |
| 4,658,809 A | 4/1987 | Ulrich et al. |
| 4,696,290 A | 9/1987 | Steffee |
| 4,719,905 A | 1/1988 | Steffee |

(Continued)

FOREIGN PATENT DOCUMENTS

DE   867422   2/1953

(Continued)

OTHER PUBLICATIONS

Kaneda, Kiyoshi et al., DePuy AcroMed Brochure "Kaneda SR Anterior Spinal System," Surgical Technique, pp. 1-11, 1999.

(Continued)

*Primary Examiner*—Eduardo C. Robert
*Assistant Examiner*—Richard Shaffer
(74) *Attorney, Agent, or Firm*—Nutter, McClennen & Fish LLP (57) ABSTRACT

An implantable medical connector device is provided that employs a snap-on technology to safely and easily mate with another device. The medical connector device generally includes an elongate member having first and second connectors members formed on opposed ends thereof. Each connector member includes an opening formed in a sidewall thereof and extending into a nesting seat. The nesting seat is adapted to seat and engage an implanted cylindrical element.

37 Claims, 7 Drawing Sheets

U.S. PATENT DOCUMENTS

| | | |
|---|---|---|
| 4,763,644 A | 8/1988 | Webb |
| 4,771,767 A | 9/1988 | Steffee |
| 4,773,402 A * | 9/1988 | Asher et al. .................. 606/61 |
| 4,805,602 A | 2/1989 | Puno et al. |
| 4,815,453 A | 3/1989 | Cotrel |
| 4,887,595 A | 12/1989 | Heinig et al. |
| 4,913,134 A | 4/1990 | Luque |
| 4,950,269 A | 8/1990 | Gaines, Jr. |
| 4,957,495 A | 9/1990 | Kluger |
| 5,002,542 A | 3/1991 | Frigg |
| 5,005,562 A * | 4/1991 | Cotrel ........................ 606/61 |
| 5,010,879 A | 4/1991 | Moriya et al. |
| 5,024,213 A | 6/1991 | Asher et al. |
| 5,030,220 A | 7/1991 | Howland |
| 5,067,955 A | 11/1991 | Cotrel |
| 5,084,049 A | 1/1992 | Asher et al. |
| 5,092,893 A | 3/1992 | Smith |
| 5,102,412 A | 4/1992 | Rogozinski |
| 5,113,685 A | 5/1992 | Asher et al. |
| 5,116,334 A | 5/1992 | Cozad et al. |
| 5,120,171 A | 6/1992 | Lasner |
| 5,127,912 A | 7/1992 | Ray et al. |
| 5,129,900 A | 7/1992 | Asher et al. |
| 5,133,716 A | 7/1992 | Plaza |
| 5,147,359 A | 9/1992 | Cozad et al. |
| 5,147,360 A | 9/1992 | Dubousset |
| 5,154,718 A | 10/1992 | Cozad et al. |
| 5,176,678 A | 1/1993 | Tsou |
| 5,176,680 A | 1/1993 | Vignaud et al. |
| 5,190,543 A | 3/1993 | Schlapfer |
| 5,207,678 A | 5/1993 | Harms et al. |
| 5,234,431 A | 8/1993 | Keller |
| 5,242,443 A * | 9/1993 | Kambin ........................ 606/60 |
| 5,261,907 A | 11/1993 | Vignaud et al. |
| 5,261,913 A | 11/1993 | Marnay |
| 5,275,600 A | 1/1994 | Allard et al. |
| 5,282,801 A | 2/1994 | Sherman |
| 5,304,177 A | 4/1994 | Pennig |
| 5,306,275 A * | 4/1994 | Bryan ........................ 606/61 |
| 5,312,405 A | 5/1994 | Korotko et al. |
| 5,330,473 A | 7/1994 | Howland |
| 5,334,203 A | 8/1994 | Wagner |
| 5,360,431 A | 11/1994 | Puno et al. |
| 5,368,594 A | 11/1994 | Martin et al. |
| 5,395,370 A | 3/1995 | Muller et al. |
| 5,403,316 A | 4/1995 | Ashman |
| 5,419,522 A | 5/1995 | Luecke |
| 5,423,818 A | 6/1995 | Van Hoeck et al. |
| 5,437,671 A | 8/1995 | Lozier et al. |
| 5,439,463 A | 8/1995 | Lin |
| 5,454,812 A | 10/1995 | Lin |
| 5,470,333 A | 11/1995 | Ray |
| 5,476,462 A | 12/1995 | Allard et al. |
| 5,487,742 A | 1/1996 | Cotrel |
| 5,496,321 A | 3/1996 | Puno et al. |
| 5,498,263 A | 3/1996 | DiNello et al. |
| 5,514,132 A | 5/1996 | Csernatony et al. |
| 5,522,816 A | 6/1996 | Dinello et al. |
| 5,527,314 A | 6/1996 | Brumfield et al. |
| 5,531,745 A | 7/1996 | Ray |
| 5,534,002 A | 7/1996 | Brumfield et al. |
| 5,549,607 A | 8/1996 | Olson et al. |
| 5,562,662 A | 10/1996 | Brumfield et al. |
| 5,562,663 A | 10/1996 | Wisnewski et al. |
| 5,582,612 A | 12/1996 | Lin |
| 5,584,831 A | 12/1996 | McKay |
| 5,586,983 A | 12/1996 | Sanders et al. |
| 5,591,165 A | 1/1997 | Jackson |
| 5,601,552 A * | 2/1997 | Cotrel ........................ 606/61 |
| 5,609,592 A | 3/1997 | Brumfield et al. |
| 5,616,142 A | 4/1997 | Yuan et al. |
| 5,620,444 A | 4/1997 | Assaker |
| 5,624,442 A | 4/1997 | Mellinger et al. |
| 5,630,816 A | 5/1997 | Kambin |
| 5,651,789 A | 7/1997 | Cotrel |
| 5,662,653 A | 9/1997 | Hattori et al. |
| 5,667,506 A | 9/1997 | Sutterlin |
| 5,667,507 A * | 9/1997 | Corin et al. .................. 606/61 |
| 5,669,910 A | 9/1997 | Korhonen et al. |
| 5,676,703 A | 10/1997 | Gelbard |
| 5,683,393 A | 11/1997 | Ralph |
| 5,688,272 A | 11/1997 | Montague et al. |
| 5,700,292 A | 12/1997 | Margulies |
| 5,704,936 A | 1/1998 | Mazel |
| 5,707,372 A | 1/1998 | Errico et al. |
| 5,709,684 A | 1/1998 | Errico et al. |
| 5,709,685 A * | 1/1998 | Dombrowski et al. ........ 606/61 |
| 5,716,355 A | 2/1998 | Jackson et al. |
| 5,743,907 A | 4/1998 | Asher et al. |
| 5,743,911 A | 4/1998 | Cotrel |
| 5,752,955 A | 5/1998 | Errico |
| 5,776,135 A | 7/1998 | Errico et al. |
| 5,885,284 A | 3/1999 | Errico et al. |
| 5,899,903 A | 5/1999 | Cotrel |
| 5,928,232 A | 7/1999 | Howland et al. |
| 5,947,966 A * | 9/1999 | Drewry et al. ................ 606/61 |
| 5,980,521 A | 11/1999 | Montague |
| 5,980,523 A | 11/1999 | Jackson |
| 5,989,250 A | 11/1999 | Wagner et al. |
| 5,989,251 A | 11/1999 | Nichols |
| 6,063,089 A | 5/2000 | Errico |
| 6,083,226 A | 7/2000 | Fiz |
| 6,110,173 A | 8/2000 | Thomas, Jr. |
| 6,113,600 A | 9/2000 | Drummond et al. |
| 6,126,660 A | 10/2000 | Dietz |
| 6,136,003 A | 10/2000 | Hoeck et al. |
| 6,139,548 A | 10/2000 | Errico |
| 6,171,311 B1 * | 1/2001 | Richelsoph .................. 606/61 |
| 6,217,578 B1 | 4/2001 | Crozet et al. |
| 6,234,705 B1 | 5/2001 | Troxell |
| 6,238,396 B1 | 5/2001 | Lomardo |
| 6,264,658 B1 | 7/2001 | Lee et al. |
| 6,273,888 B1 * | 8/2001 | Justis .......................... 606/61 |
| 6,283,967 B1 * | 9/2001 | Troxell et al. ................ 606/61 |
| 6,287,309 B1 | 9/2001 | Baccelli et al. |
| 6,302,882 B1 | 10/2001 | Lin |
| 6,315,779 B1 | 11/2001 | Morrison et al. |
| 6,328,741 B1 | 12/2001 | Richelsoph |
| 6,402,751 B1 | 6/2002 | Hoeck |
| 6,413,257 B1 | 7/2002 | Lin |
| 6,432,108 B1 | 8/2002 | Burgess |
| 6,524,310 B1 | 2/2003 | Lombardo |
| 6,554,832 B1 * | 4/2003 | Shluzas ...................... 606/61 |
| 6,602,253 B1 | 8/2003 | Richelsoph |
| 6,616,668 B1 | 9/2003 | Altarac et al. |
| 6,641,583 B1 | 11/2003 | Shluzas et al. |
| 6,673,073 B1 | 1/2004 | Schafer |
| 6,689,133 B1 | 2/2004 | Morrison |
| 6,736,817 B1 | 5/2004 | Troxell |
| 6,752,807 B1 | 6/2004 | Lin |
| 6,958,066 B1 | 10/2005 | Richelsoph et al. |
| 2002/0007183 A1 | 1/2002 | Lee et al. |
| 2002/0052603 A1 | 5/2002 | Nichols |
| 2002/0111625 A1 | 8/2002 | Richelsoph et al. |
| 2002/0138077 A1 | 9/2002 | Ferree |
| 2002/0143330 A1 | 10/2002 | Shluzas |
| 2002/0169448 A1 | 11/2002 | Vanacker |
| 2003/0018334 A1 | 1/2003 | Richelsoph et al. |
| 2003/0023244 A1 | 1/2003 | Richelsoph et al. |
| 2003/0028192 A1 | 2/2003 | Schar et al. |
| 2003/0045874 A1 | 3/2003 | Thomas |
| 2003/0114853 A1* | 6/2003 | Burgess et al. ............... 606/61 |
| 2003/0153917 A1 | 8/2003 | Richelsoph et al. |
| 2004/0006342 A1 | 1/2004 | Altarac et al. |

| | | | |
|---|---|---|---|
| 2004/0039385 A1 | 2/2004 | Mazda | |
| 2004/0049190 A1 | 3/2004 | Biedermann et al. | |
| 2004/0087949 A1 | 5/2004 | Bono et al. | |
| 2004/0116928 A1 | 6/2004 | Young et al. | |
| 2004/0133203 A1 | 7/2004 | Young et al. | |
| 2005/0090821 A1 | 4/2005 | Berrevoets et al. | |
| 2005/0228326 A1 | 10/2005 | Kalfas et al. | |
| 2005/0228377 A1 | 10/2005 | Chao et al. | |

FOREIGN PATENT DOCUMENTS

| | | |
|---|---|---|
| DE | 3219575 | 12/1983 |
| DE | 3639810 | 5/1988 |
| DE | 4330837 | 3/1995 |
| EP | 0128058 | 12/1984 |
| EP | 0242708 | 10/1987 |
| EP | 0820722 | 1/1998 |
| EP | 0 878 170 A2 | 11/1998 |
| EP | 0956829 | 11/1999 |
| EP | 1295566 | 3/2003 |
| FR | 2624720 | 6/1989 |
| FR | 2645427 | 10/1990 |
| FR | 2697743 | 5/1994 |
| FR | 2714590 | 7/1995 |
| FR | 2615095 | 11/1998 |
| FR | 2816195 | 5/2002 |
| FR | 2795622 | 1/2005 |
| GB | 167228 | 7/1921 |
| GB | 2173104 | 10/1986 |
| GB | 2208476 | 4/1989 |
| JP | 11-244299 | 9/1999 |
| JP | 2000-033091 | 2/2000 |
| SU | 286136 | 11/1970 |
| SU | 1823791 | 6/1993 |
| WO | WO-87/00160 | 1/1987 |
| WO | WO-90/04948 | 5/1990 |
| WO | WO-91/16020 | 10/1991 |
| WO | WO-95/13754 | 5/1995 |
| WO | WO-00/57801 | 10/2000 |
| WO | WO-00/59387 | 10/2000 |
| WO | WO-01/01872 | 1/2001 |
| WO | WO-01/24718 | 4/2001 |
| WO | WO-02/30307 | 4/2002 |

OTHER PUBLICATIONS

Betz, Randall R. et al., DePuy AcroMed Brochure, "Fronterior Anterior Deformity System," Surgical Technique, 21 pages, Aug. 2002.

DePuy AcroMed, "CrossOver CrossConnector" brochure, Apr. 2003.

Lim, et al., "Biomechanics of Transfixation in Pedicle Screw Instrumentation", SPINE, vol. 21, No. 19, pp. 2224-2229, 1996.

Martin H. Krag, "Biomechanics of Thorocolumbar Spinal Fixation," SPINE, vol. 16, No. 3, Supplement, pp. S84-S99 (1991).

Carson et al., "Internal Forces and Moments in Transpecular Spine Instrumentation", SPINE, vol. 15, No. 9; pp. 893-901.

Asher, et al., "A Modular Spinal Rod Linkage System to Provide Rotational Stability", SPINE, vol. 13, No. 3, pp. 272-277, 1998.

Bick et al., "Mechanical Evaluation of Cross-Link Designs in Rigid Pedicle Screw Systems", SPINE, vol. 22, No. 4, pp. 370-375, 1997.

"Ovation™ Polyaxial System" by Osteotech Inc. (author unknown), description downloaded from http://www.osteotech.com/prodpoly2.htm; pp. 1-6; (Oct. 28, 2003).

* cited by examiner

SNAP-ON SPINAL ROD CONNECTOR

FIELD OF THE INVENTION

The present invention relates to spinal fixation devices.

BACKGROUND OF THE INVENTION

Spinal fixation devices are used in orthopedic surgery to align and/or fix a desired relationship between adjacent vertebral bodies. Such devices typically include a spinal fixation element, such as a relatively rigid fixation rod that is coupled to adjacent vertebrae by attaching the element to various anchoring devices, such as hooks, bolts, wires, or screws. Often two rods are disposed on opposite sides of the spinous process in a substantially parallel relationship. The fixation rods can have a predetermined contour that has been designed according to the properties of the target implantation site, and once installed, the rods hold the vertebrae in a desired spatial relationship, either until desired healing or spinal fusion has taken place, or for some longer period of time.

Spinal rod connectors, also known as cross-connectors, are often used in conjunction with spinal fixation devices to provide additional stability to the devices. It has been found that when a pair of spinal rods are fastened in parallel on either side of the spinous process, the assembly can be significantly strengthened by using at least one additional rod to bridge the pair of spinal rods. The connectors are typically in the form of rod having a clamp formed on each end thereof for mating with a spinal rod.

While current spinal rod connectors have proven effective, difficulties have been encountered in mounting the connectors, and maintaining them in a desired position and orientation with respect to the spinal rod. In particular, the clamp assemblies often consist of several parts which increase the manufacturing costs and make surgical application tedious. Since the cross-connector is often applied as the last step in a lengthy surgical procedure, ease of application is paramount. Moreover, some current devices tend to be bulky, which can cause irritation to the patient's back muscles and other tissue that might impinge on the device.

Accordingly, there presently exists a need for an improved spinal connector that can be easily installed and that securely mates two spinal rods. There is also a need for a device having a low-profile to avoid potential irritation and injury to the patient.

SUMMARY OF THE INVENTION

The present invention generally provides an implantable medical connector device, or cross-connector, that is effective to connect between two substantially parallel spinal fixation devices. The medical connector device generally includes an elongate member having a longitudinal axis, and first and second ends. First and second connector members are formed on the first and second ends, and each connector member includes a width extending transverse to the longitudinal axis of the elongate member, an opening formed in a sidewall thereof and oriented substantially transverse to the longitudinal axis, and a nesting seat formed in the connector member and in communication with the opening. The nesting seat preferably has a substantially circular shape and is adapted to seat and engage an implanted cylindrical element.

In one embodiment, the first and second connector members each have a generally circular shape, and the opening of each connector member has a dimension that is less than a diameter of the nesting seat of each connector member. However, the dimension of the opening is expandable in response to the insertion of an implanted cylindrical element therein. Preferably, the dimension of the opening in each of the first and second connector members decreases from an outer surface of the connector member to an inner wall of the nesting seat. The opening can be positioned anywhere around the circumference of the first and second connector members, but preferably the opening in each of the first and second connector members is oriented at an angle toward a midregion of the elongate member. More preferably, the opening in each of the first and second connector members extends at an angle in the range of about 30° to 90° relative to the longitudinal axis of the elongate member.

In another embodiment, the first and second connector members can be coplanar with the elongate member, and each connector member can have a height that is substantially the same as or greater than a height of the elongate member. The width of each connector member can also vary, but preferably the width of each connector member is greater than the width of the elongate member. The sidewall of each connector member preferably includes a thickness that decreases from the portion of the sidewall adjacent to the elongate member to the portion of the sidewall farthest from the elongate member.

In other aspects, a spinal rod and connector system is provided having at least one rigid elongate cylindrical rod, and at least one connector member having an elongate portion with first and second ends. Each end of the elongate portion has a substantially C-shaped sidewall defining an opening extending into a nesting seat adapted to seat and engage a rigid elongate cylindrical rod. The opening formed in each end preferably has a dimension less than a diameter of the nesting seat. The dimension of the opening, however, is preferably expandable in response to insertion of a rigid elongate cylindrical rod therein. The elongate portion of the connector member can be semi-flexible such that, upon rotation of a rigid elongate cylindrical rod disposed within the ends of the connector member, the elongate portion distorts to prevent the rigid elongate cylindrical rod from disengaging with the connector member.

The present invention also provides an implantable medical connector kit including a plurality of connector members having an elongate portion having a length and first and second ends. Each end has a substantially C-shaped sidewall defining an opening extending into a nesting seat adapted to seat and engage a rigid elongate cylindrical rod. The dimension of the opening in each end of each of the plurality of connector members is expandable in response to insertion of a rigid elongate cylindrical rod therein. In a preferred embodiment, the elongate portion of each of the plurality of connector members has a length different from the length of the elongate portion of another one of each of the plurality of connector members. Alternatively, or in addition, the elongate portion of each of the plurality of connector members can have radius of curvature different from the radius of curvature of the elongate portion of another one of each of the plurality of connector members.

BRIEF DESCRIPTION OF THE DRAWINGS

The invention will be more fully understood from the following detailed description taken in conjunction with the accompanying drawings, in which.

DETAILED DESCRIPTION OF THE INVENTION

In general, the present invention provides an implantable medical connector device that employs a snap-on design to safely and easily mate with another device. The connector can be used for a variety of applications, but is preferably a cross-connector effective to mate two adjacent, parallel spinal rods in a spinal fixation system. The connector is preferably formed from a single piece that provides a secure connection without the need for additional locking elements. Moreover, the device can have a low-profile shape to avoid tissue abrasion. The device is particularly advantageous in that the use of a single, low-profile cross-connector having a snap-on design reduces manufacturing costs, is easy to implant, and reduces the risk of damage to tissue surrounding the device.

Figure 1:
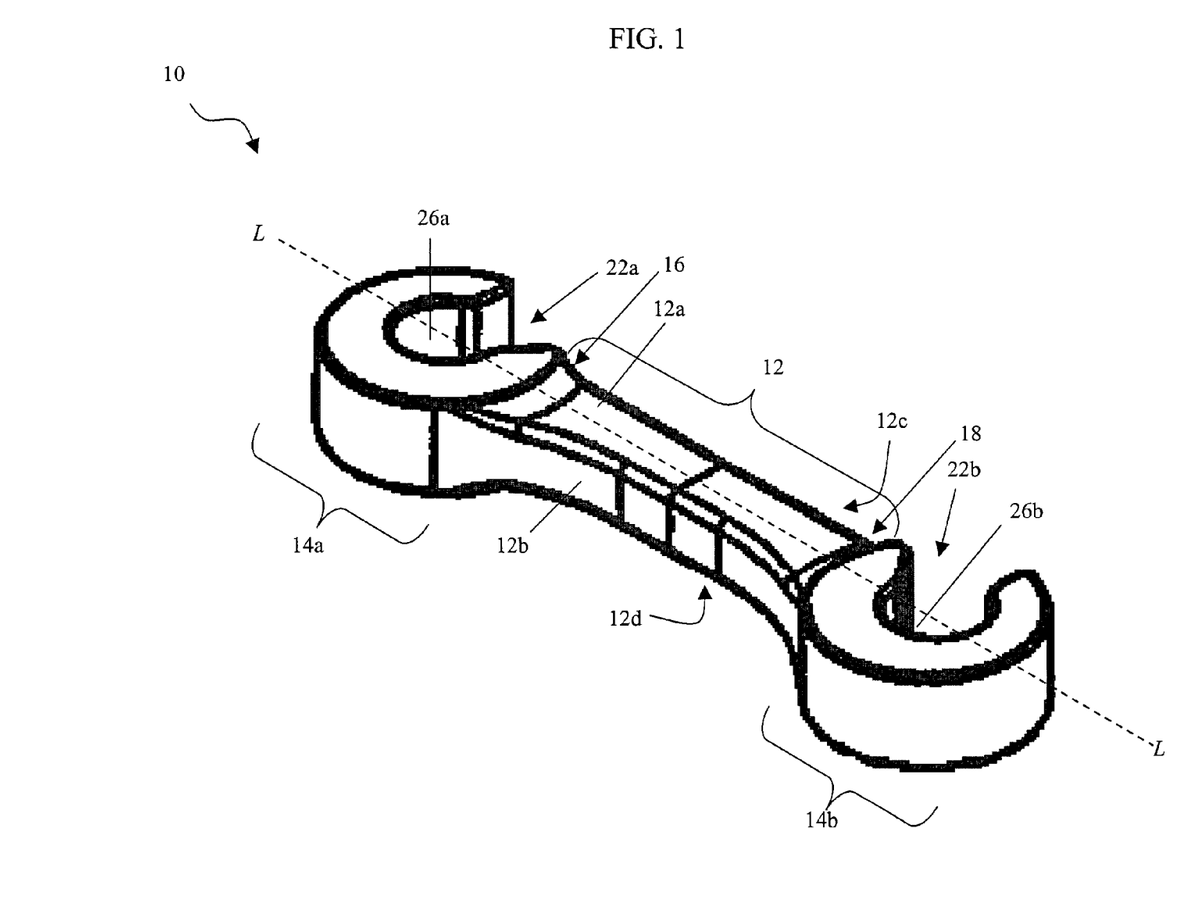
FIG. 1 is a perspective view of a medical connector device according to one embodiment of the present invention.
Figure 2:
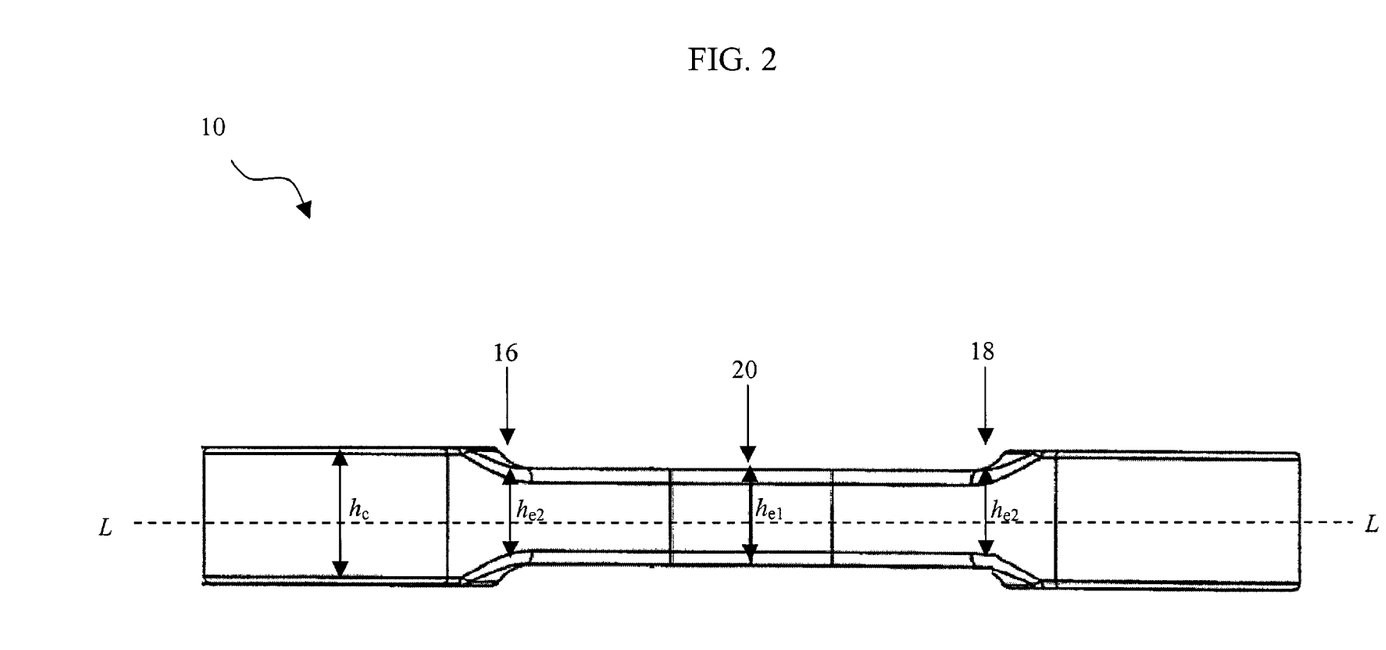
FIG. 2 is a side view illustration of the medical connector device shown in FIG. 1.
Figure 3:
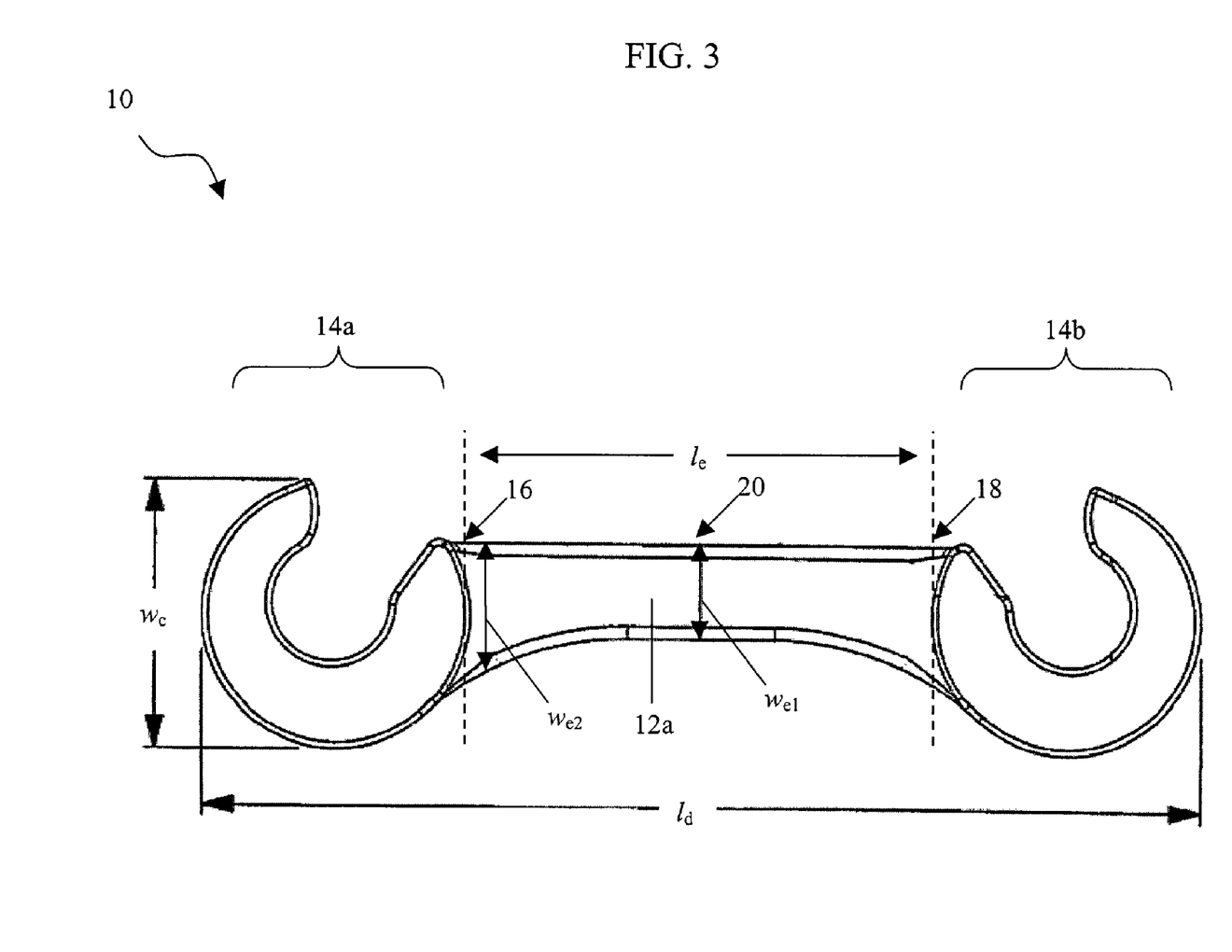
FIG. 3 is a top view illustration of the medical connector device shown in FIGS. 1 and 2.

As shown in FIGS. 1–3, the medical connector device 10, hereinafter referred to as a cross-connector, generally includes an elongate member 12 having first and second connectors members 14a, 14b formed on opposed ends 16, 18 thereof. Each connector member 14a, 14b includes an opening 22a, 22b formed in a sidewall thereof and extending into a nesting seat 26a, 26b. The nesting seat 26a, 26b is adapted to seat and engage an implanted cylindrical element.

The elongate portion 12 of the cross-connector 10 can have a variety of configurations, but preferably has a low-profile shape to avoid potential damage to tissue adjacent the implant site. Moreover, the elongate member is preferably sufficiently rigid to securely mate with a spinal rod or similar medical device. The elongate member 12 can, however, have some degree of flexibility to allow distortion or flexation thereof to prevent the connector members from becoming disengaged. FIGS. 1–3 illustrate an exemplary embodiment of an elongate member 12 having four sides 12a, 12b, 12c, 12d which define a generally rectangular cross-section. A person having ordinary skill in the art will appreciate that, while a generally rectangular cross-section is shown, the elongate member 12 can have any cross-sectional shape, including square, triangular, and circular. The sides 12a–12d extend along a length $l_e$ (FIG. 3) of the elongate member 12, and include a midregion 20 and opposed ends 16, 18. The sides 12a–12d can be substantially planar, or can be curved depending on the intended use. For example, the elongate member 12 can be curved along the longitudinal axis L of the device 10 to match the contour of a patient's spinal column.

The dimensions of the elongate member 12 can also vary, and will depend on the intended use. The length $l_e$ of the elongate member 12 should, however, be sufficient to extend between two spinal rods that are secured on opposite sides of a patient's spinal column. Preferably, the length $l_e$ of the elongate member 12 is between about 10 mm and 150 mm. The elongate member 12 can, however, be adapted to have an adjustable length, as will be described in more detail with respect to FIGS. 5 and 6.

The elongate member 12 further includes a width $W_c$ and height. As shown in FIGS. 2 and 3, opposed longitudinal sides 12a, 12c define a width $W_e$ (FIG. 3), and opposed longitudinal sides 12b, 12d define a height (FIG. 2) of the elongate member 12. The width $W_e$, and height can be substantially the same or they can vary along the length $l_e$ of the elongate member 12. As shown in FIG. 3, the width $W_e$ of the elongate member 12 is greater than the height $h_e$, and the length $l_o$ of the elongate member 12 is greater than both the width $W_c$ and height. In an exemplary embodiment, the width $W_{e1}$ at the midregion 20, and along a substantial portion of the length $l_e$ of the elongate member 12, is less than the width $W_{e2}$ at the ends 16, 18 of the elongate member 12, as shown in FIG. 2. The height $h_{e1}$ at the midregion 20 of the elongate member 12 is also preferably the same along a substantial portion of the length $l_e$ of the member 12, and the height $_{e2}$ at the ends 16, 18 is preferably greater than the height $h_{e1}$ at the midregion 20. The increased width $W_{e2}$ and height $h_{e2}$ of the elongate member 12 adjacent the ends 16, 18 will result in a more narrow midregion 20 and thicker ends 16, 18. The narrow midregion 20 is particularly advantageous to allow for some distortion or flexation of the elongate member at the midregion 20, and the thicker ends 16, 18 provide a more secure connection with the connector members 14a, 14b. The flexibility of the midregion can also be controlled not only by the geometry of the elongate member 12, but also by the material used to form the elongate member 12. In an exemplary embodiment the width $W_{e1}$ at the midregion 20 is between about 3 mm and 8 mm, the width $W_{e2}$ at the ends 16, 18 is between about 4 mm and 10 mm, the height $h_{e1}$ at the midregion 20 is between about 3 mm and 10 mm, and the height $h_{e2}$ at the ends 16, 18 is between about 5 mm and 15 mm.

Figure 4:
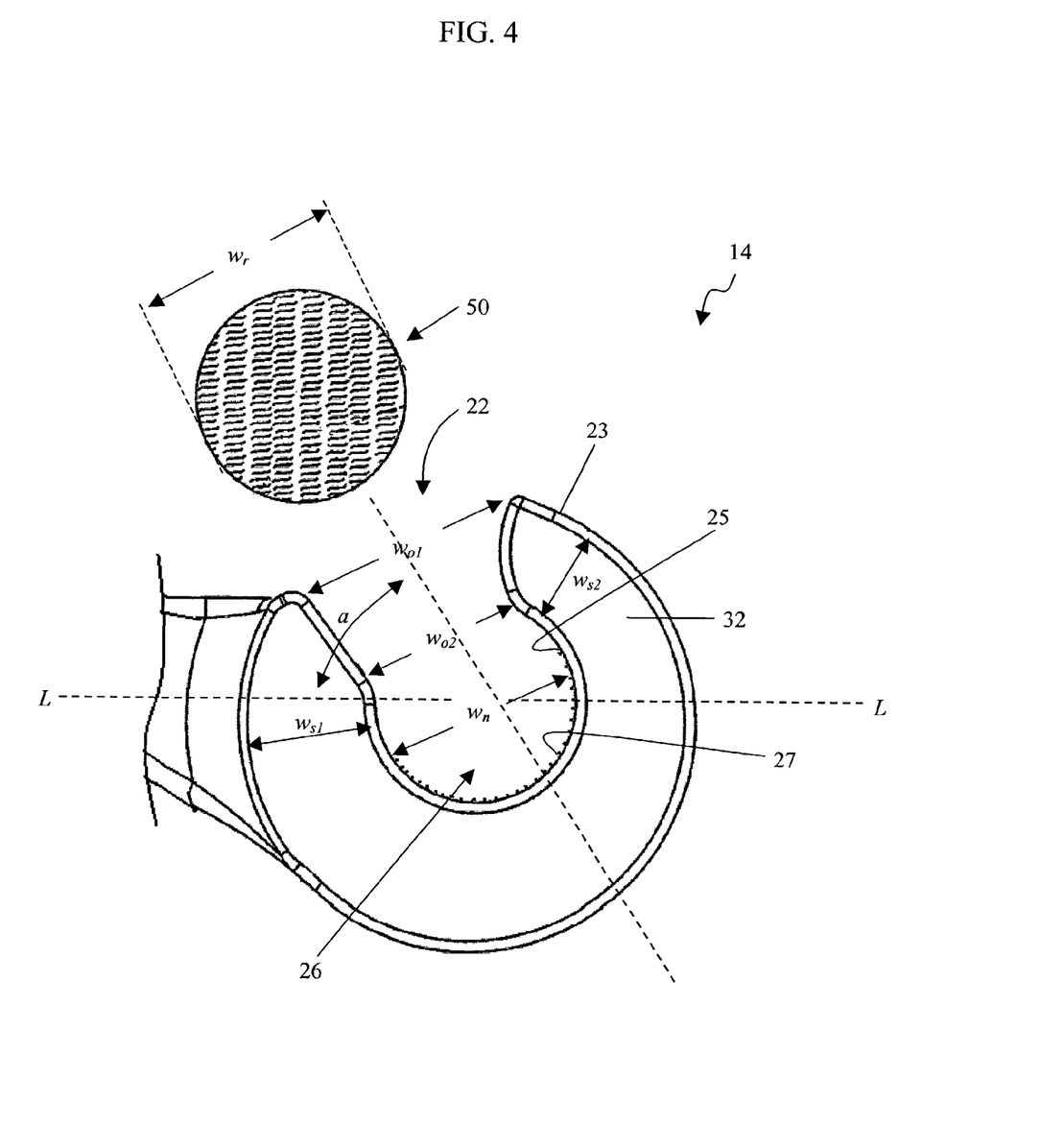
FIG. 4 is an enlarged view of a connector portion of the medical connector device shown in FIGS. 1–3 positioned adjacent a spinal rod.

A connector member 14, which is mated to or formed on one end of the elongate member 12, is shown in more detail in FIG. 4. Since each connector member 14a, 14b is preferably identical, FIG. 4 is illustrative of both connector members 14a, 14b shown in FIGS. 1–3. The connector member 14 can be mated to the elongate member 12 using a variety of mating techniques, but preferably the connector member 14 is integrally formed with the elongate member 12. The connector member 14 can have a variety of shapes and sizes, but should be adapted to snap-on to a spinal rod or similar cylindrical member and remain mated thereto under physiological loads applied to the cross-connector 10.

While the shape and size can vary, FIG. 4 illustrates a connector member 14 having a substantially C-shaped sidewall 32 with an opening 22 formed therein. The sidewall 32 has a width $W_{S1}$ adjacent the side of the opening 22 positioned near the elongate member 12 that decreases to a width $W_{S2}$ adjacent the side of the opening 22 positioned farthest away from the elongate member 12. The decreasing width allows the narrower portion, e.g., the portion of the sidewall positioned farthest away from the elongate member 12, to have a greater degree of flexibility and to thereby minimize stress concentration. The opening 22 can be positioned anywhere in the sidewall 32, but is preferably positioned so as to be transverse to the longitudinal axis L. The angle of the opening 22 is preferably optimized to provide maximum resistance to sagittal and coronal plane applied movements. More preferably, the opening 22 is positioned at an angle $\alpha$ with respect to the longitudinal axis L of the device. More preferably, the opening 22 extends toward the midregion 20 of the elongate member 12, and is positioned at an angle α between about 30° and 90° relative to the longitudinal axis L. The opening 22 extends into a circular nesting seat 26 which is adapted to seat and engage a cylindrical spinal rod 50. The width $W_n$ of the nesting seat 26 should be adapted to provide an interference fit and maximum contact with a rod 50 that may be disposed therein. Since the nesting seat 26 is sized to engage the cylindrical rod 50, the opening 22 should have a width $W_o$ less than a width $W_n$ of the nesting seat 26 and less than the width $W_r$ of the rod 50 to secure the rod 50 therein. Preferably, the opening 22 is optimized to provide maximum grip strength of a rod 50 disposed therein, yet does not hinder insertion of the rod 50 through the opening 22. Moreover, the width $W_o$ of the opening 22 can vary from the outer surface 23 to the inner surface 25 of the connector member 14. To facilitate insertion of the cylindrical spinal rod 50 into the nesting seat 26, the opening 22 can have an outer width $W_{o1}$ greater than an inner width $W_{o2}$. The outer width $w_{o1}$ should, however, be less or substantially the same as the width $W_n$ of the nesting seat 26. In an exemplary embodiment, the width $W_{s1}$ of the sidewall 32 adjacent the elongate member 12 is between about 3 mm and 8 mm, and the width $W_{s2}$ of the sidewall 32 farthest away from the elongate member 12 is between about 2 mm and 6 mm. Moreover, the outer width $W_{o1}$ of the opening 22 is preferably between about 3.5 mm and 8mm, the inner width $W_{o2}$ of the opening 22 is preferably between about 2 mm and 6 mm, and the width $W_n$ of the nesting seat 26 is preferably between about 2.5 mm and 6.5 mm. The connector member 14 can also have a height $h_c$ that is greater than a height of the elongate member 12, and a width $W_5$ that is greater than a width of the elongate member 12.

In another embodiment, the inner surface nesting seat 26 can include one or more surface features 27 to inhibit movement of the rod 50 once seated therein. The surface features 27 can be integrally formed within the nesting seat 26, or can be disposed thereon. The surface features 27 can have any shape and size, and can be formed from a variety of materials. By way of non-limiting example, the surface features 27 can be formed from ridges or protrusions disposed on the surface of the nesting seat 26. Alternatively, or in addition, a non-slip or gripping material can be disposed on the nesting seat 26, and/or the nesting seat can have a knurled surface. A person having ordinary skill in the art will appreciate that a variety of techniques can be used to inhibit movement between the rod 50 and the nesting seat 26.

Figure 5:
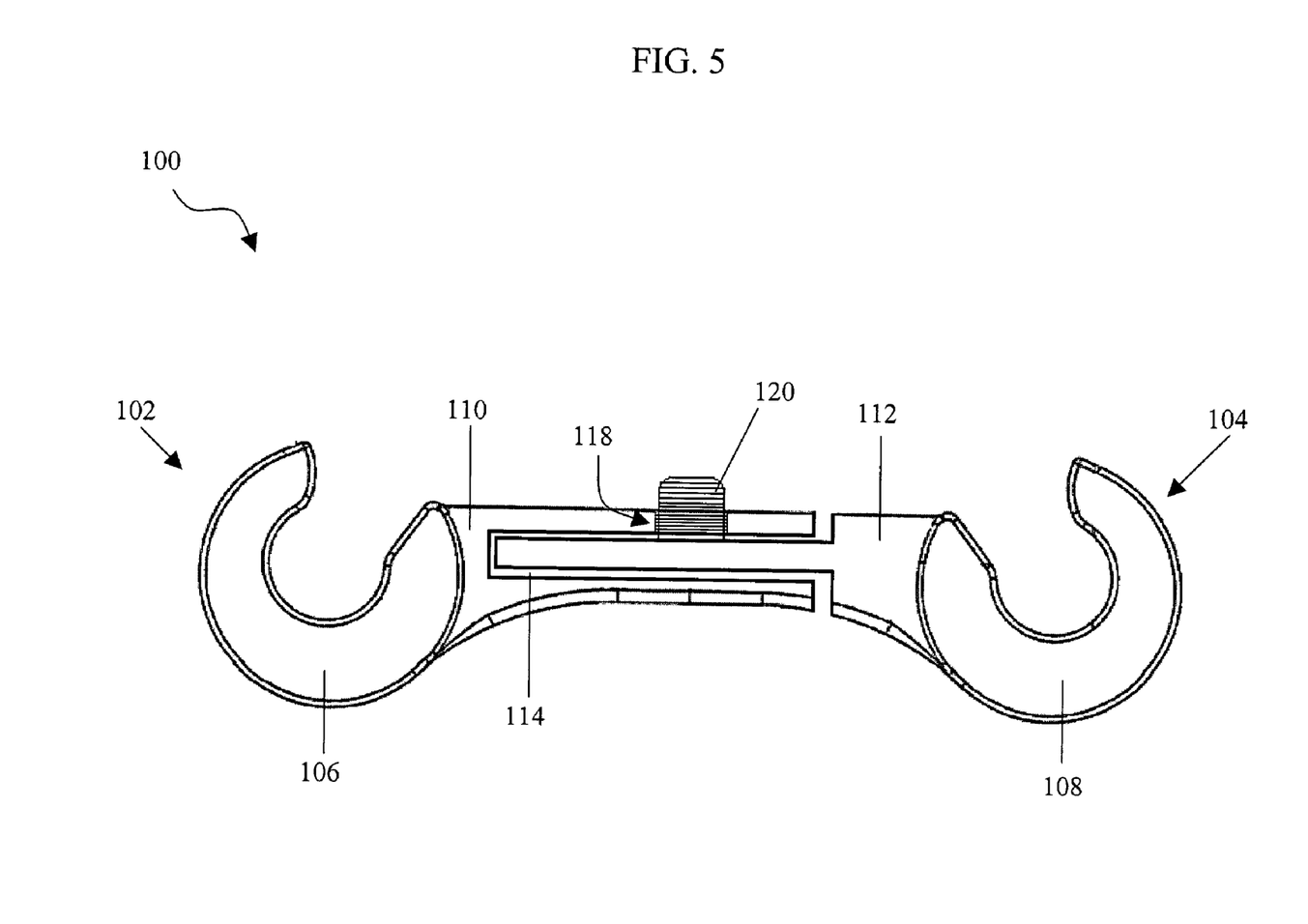
FIG. 5 is a perspective view of a medical connector device according to another embodiment of the present invention.
Figure 6:
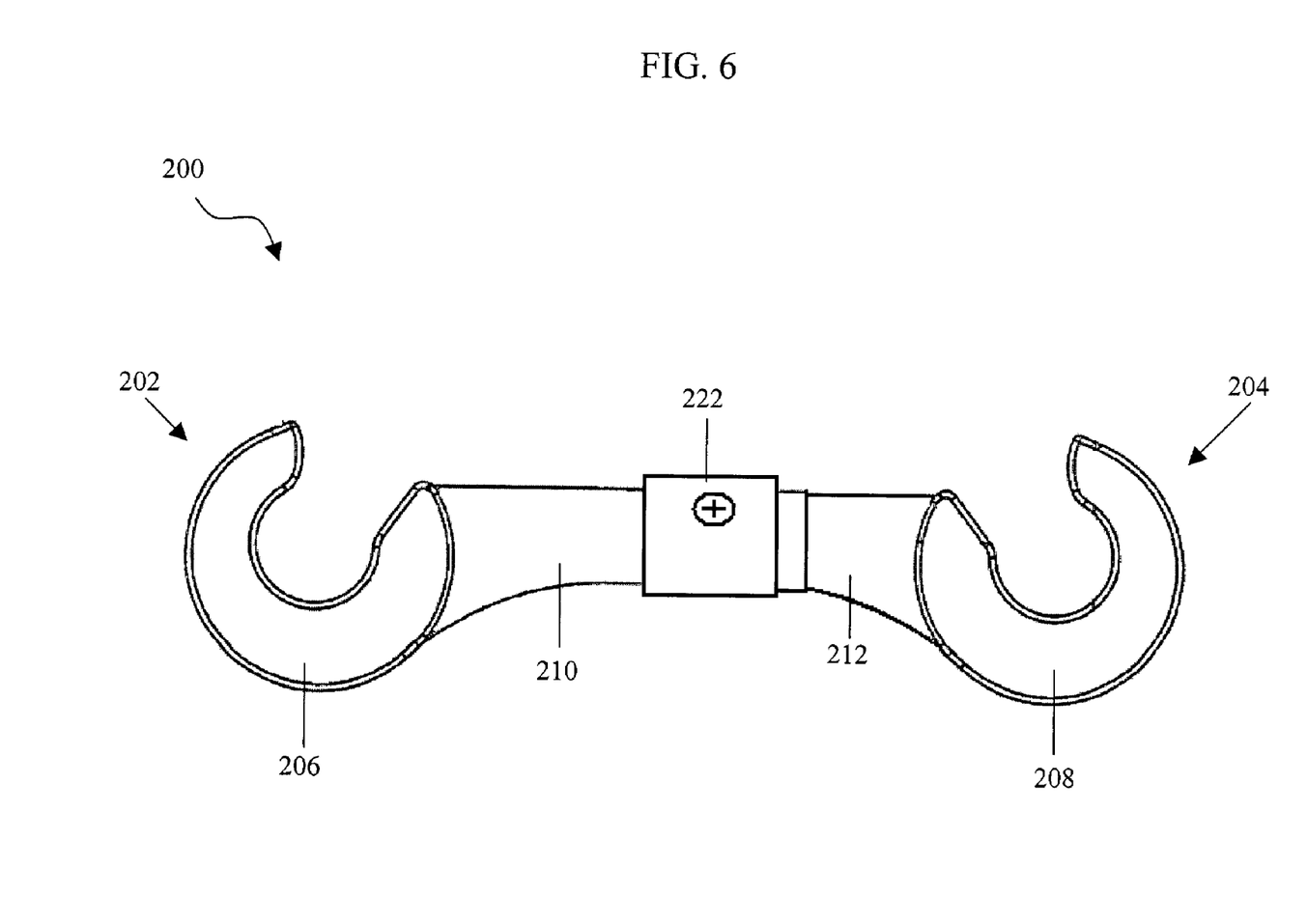
FIG. 6 is a perspective view of yet another embodiment of a medical connector device of the present invention.

FIGS. 5 and 6 illustrate additional embodiments of a cross-connector 100, 200 according to the present invention. Devices 100, 200 are similar to device 10, but are adapted to have an adjustable length. As shown in FIG. 5, the cross-connector 100 includes first and second components 102, 104, each of which has a connector member 106, 108 and an elongate member 110, 112. The elongate member 110 of component 102 includes a channel 114 formed therein for slidably receiving corresponding elongate member 112 of component 104. In use, the components 102, 104 can be moved with respect to each other to adjust the length of the device 100. A locking element can optionally be provided for preventing movement of the components 102, 104 with respect to each other once the desired length is set. While a variety of locking elements can be used, FIG. 5 illustrates one embodiment of a suitable locking element having a threaded bore 118 formed in component 102 and adapted to receive a locking screw 120. The locking screw 120, when fully threaded into the bore 118, is adapted to prevent component 104 from moving with respect to component 102. The distal surface of the locking screw 120 can include an compressible material disposed thereon and adapted to grip component 104 to prevent movement thereof. Alternatively, or in addition, component 104 can include several threaded bores (not shown) formed therein for receiving the distal end of the threaded screw 120, or the locking screw 120 can merely provide an interference fit with component 104 to prevent movement thereof.

FIG. 6 illustrates another embodiment of a connector 200 having an adjustable length. As shown, the connector 200 includes first and second components 202, 204, each having a connector portion 206, 208 and an elongate portion 210, 212. The elongate portion 210 of the first component 202 is hollow to slidably receive the elongate portion 212 of the second component 204. A clamp 222 is disposed around the components 202, 204 and, when tightened, is effective to prevent movement of the components 202, 204 with respect to one another.

A person having ordinary skill in the art will appreciate that FIGS. 5 and 6 are merely exemplary embodiments of cross-connector devices having an adjustable length, and that a variety of techniques can be used to provide such a device.

Figure 7:
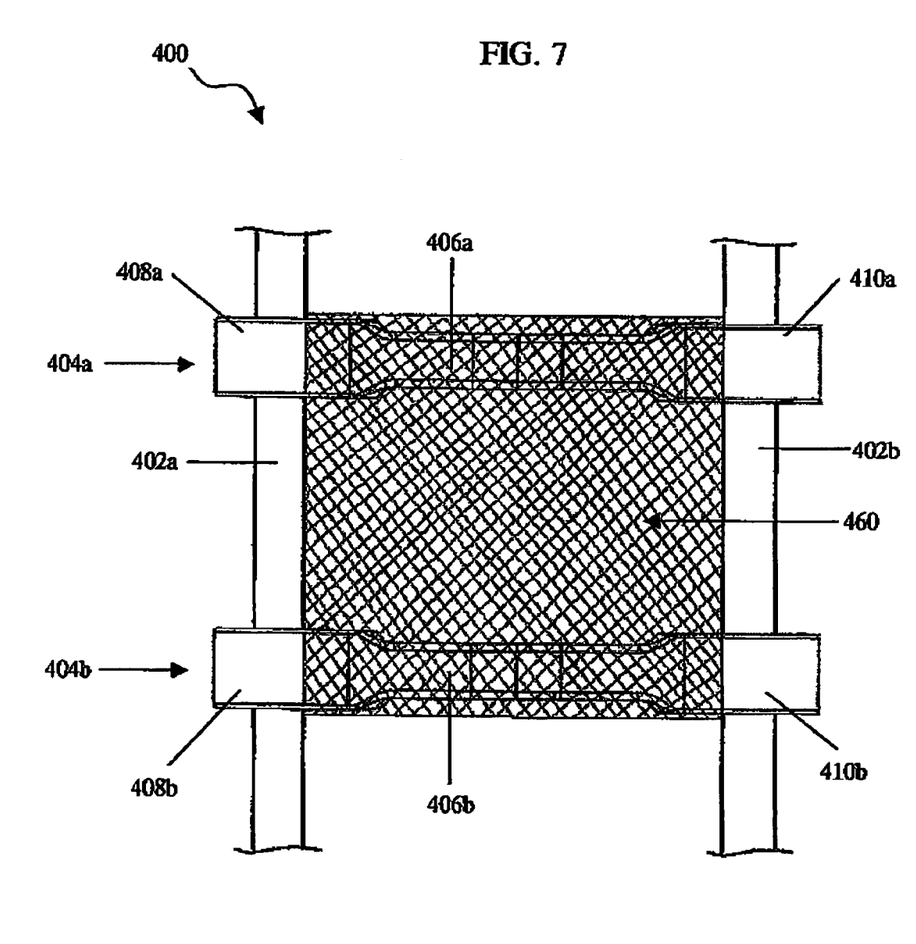
FIG. 7 is top view illustration of a spinal rod system according to yet another embodiment of the present invention.

In another embodiment of the present invention, a protective sheath can be disposed around at least a portion of the cross-connector. FIG. 7 illustrates a spinal rod connector system 400 having first and second elongate cylindrical rods 402a, 402b, and first and second cross-connector devices 404a, 404b mated to the first and second rods 402a, 402b. Each cross-connector device 404a, 404b includes an elongate portion 406a, 406b, and first and second connector portions 408a, 408b, 410a, 410b disposed on opposed ends of the elongate portion 406a, 406b. The connector portions 408a, 408b, 410a, 410b are disposed around and engage the elongate rods 402a, 402b. The system 400 further includes a protective sheath 460 that extends around and between the elongate portion 406a, 406b of each connector member 404a, 404b. The sheath 460 can be attached to the connectors 404a, 404b using a variety of mating elements, such as sutures. The sheath 460 is effective to protect the spine, and can be formed from a variety of materials. Preferably, the sheath 460 is formed from a flexible, synthetic or biological material. In another embodiment, a single sheath (not shown) can be disposed around only one cross-connector. A person having ordinary skill in the art will appreciate that the sheath can have a variety of configurations, but should be adapted to prevent damage to tissue surrounding the connector, particularly to shield the spinal canal.

The present invention can be provided as a single component, or can be provided as a medical connector kit having several cross-connectors. The kit preferably includes cross-connectors having varying lengths to allow the surgeon to select an appropriately sized cross-connector. The cross-connectors can also or alternatively have an elongate portion with a radius of curvature different from the radius of curvature of the elongate portion of another one of the connectors in the kit.

The cross-connectors according to the present invention can be formed from a variety of materials. Suitable materials include medical grade plastics, fiber-reinforced polymers, stainless steel, titanium, bioabsorbable polymers, shape memory materials, and combinations thereof. The material can be rigid, semi-rigid, or flexible. Examples of suitable polymers include polyether sulfone, polycarbonate, and bioabsorbable polymers, and examples of suitable composites include carbon fiber reinforced polymers. Examples of suitable malleable materials include stainless steel and titanium.

In one embodiment, the material is a thermoplastic polymer with a glass transition temperature (Tg) whereby upon heating to a temperature above Tg, the material becomes malleable and will hold its shape upon cooling below Tg. In an exemplary embodiment, the cross-connector is formed from a shape-memory material, such as Nitinol. This allows the connector portions to expand to receive the rod, and return to the original shape whereby the rod is engaged by the connector.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implantable medical connector device, comprising:
   an elongate member having a length extending along a longitudinal axis, and first and second ends; and
   first and second connector members formed on the first and second ends, each connector member having
      a width extending transverse to the longitudinal axis of the elongate member,
      an opening formed in a sidewall thereof and oriented substantially transverse to the longitudinal axis, and
      a nesting seat formed in the connector member and in communication with the opening, the nesting seat having a substantially circular shape and being adapted to snap-on to and engage an implanted cylindrical element, and having a diameter greater than a dimension of the opening;
   wherein the elongate member is semi-flexible such that, upon rotation of a rigid elongate cylindrical rod disposed within the first and second connector members, the elongate member distorts to prevent the rigid elongate cylindrical rod from disengaging with the first and second connector members.

2. The device of claim 1, wherein the dimension of the opening in each of the first and second connector members decreases from an outer surface of the connector member to an inner wall of the nesting seat.

3. The device of claim 1, wherein the dimension of the opening is expandable in response to the insertion of an implanted cylindrical element therein.

4. The device of claim 1, wherein an inner wall of the nesting seat of at least one of the first and second connector members includes surface features effective to inhibit movement of an implanted cylindrical element seated within the nesting seat.

5. The device of claim 1, wherein the first and second connector members each have a generally circular shape.

6. The device of claim 1, wherein the opening in each of the first and second connector members is oriented at an angle toward a midregion of the elongate member.

7. The device of claim 6, wherein the opening in each of the first and second connector members extends at an angle in the range of about 30° to 90° relative to the longitudinal axis of the elongate member.

8. The device of claim 1, wherein the elongate member has a height substantially the same as or less than the height of each of the connector members.

9. The device of claim 1, wherein the width of each connector member is greater than a width of the elongate member.

10. The device of claim 1, wherein the first and second connector members are coplanar with the elongate member.

11. The device of claim 1, wherein the sidewall of each connector member includes a thickness that decreases from an inner portion of the sidewall adjacent the elongate member to an outer portion of the sidewall opposed to the inner portion.

12. The device of claim 1, wherein the first and second connector members are integrally formed with the elongate member.

13. The device of claim 1, wherein the elongate member is curved.

14. The device of claim 1, wherein the elongate member has an adjustable length.

15. The device of claim 1, wherein the elongate member comprises first and second portions slidably movable with respect to each other.

16. The device of claim 1, further comprising a protective sheath disposed on at least a portion of the device.

17. The device of claim 1, wherein the first and second connector members are formed from a shape memory material.

18. The device of claim 1, wherein the device is formed from materials selected from the group consisting of medical grade plastics, fiber-reinforced polymers, stainless steel, titanium, bioabsorbable polymers, shape memory materials, and combinations thereof.

19. The device of claim 1, wherein the device is formed from Nitinol.

20. A spinal rod and connector system, comprising:
   at least one rigid elongate cylindrical rod;
   at least one connector member having an elongate portion with first and second ends, each end having a substantially C-shaped sidewall defining an opening extending into a nesting seat wherein the opening in each connector member has a dimension less than a diameter of the nesting seat, and each connector member being adapted to snap-on to and engage a rigid elongate cylindrical rod, and wherein the elongate portion of the connector member is semi-flexible such that, upon rotation of a rigid elongate cylindrical rod disposed within a connector member, the elongate portion distorts to prevent the rigid elongate cylindrical rod from disengaging with the connector member.

21. The system of claim 20, wherein the dimension of the opening is expandable in response to insertion of a rigid elongate cylindrical rod therein.

22. The system of claim 20, wherein the opening in each of the first and second connector members is oriented at an angle toward a midregion of the elongate portion.

23. The system of claim 22, wherein the opening in each of the first and second connector members extends at an angle in the range of about 30° to 90° relative to a longitudinal axis of the elongate portion.

24. The system of claim 20, wherein the elongate portion has a height substantially the same as or less than a height of each of the connector members.

25. The system of claim 20, wherein the first and second connector members are coplanar with the elongate portion.

26. The system of claim 20, wherein the elongate cylindrical rod is curved.

27. The system of claim 20, wherein the elongate cylindrical rod has an adjustable length.

28. The system of claim 27, wherein the elongate cylindrical rod comprises first and second portions slidably movable with respect to each other.

29. The system of claim 20, wherein the system further comprises a protective sheath disposed on at least a portion of the device.

30. The system of claim 20, wherein the sidewall of each connector member includes a thickness that decreases from an inner portion of the sidewall adjacent the elongate portion to an outer portion of the sidewall opposed to the inner portion.

31. The system of claim 20, wherein the first and second connector members are formed from a shape memory material.

32. The system of claim 20, wherein the device is formed from materials selected from the group consisting of medical grade plastics, fiber-reinforced polymers, stainless steel, titanium, bioabsorbable polymers, shape-memory polymers, and combinations thereof.

33. The system of claim 20, wherein the device is formed from Nitinol.

34. An implantable medical connector kit, comprising:
a plurality of connector members having an elongate portion having a length and first and second ends, each end having a substantially C-shaped sidewall defining an opening extending into a nesting seat adapted to snap-on to and engage a rigid elongate cylindrical rod without the use of a locking mechanism, a least a portion of each connector member being semi-flexible such that, upon rotation of a rigid elongate cylindrical rod disposed within an end of the connector, the connector member distorts to prevent the rigid elonoate cylindrical rod from disengaging with the end of the connector.

35. The kit of claim 34, wherein the dimension of the opening in each end of each of the plurality of connector members is expandable in response to insertion of a rigid elongate cylindrical rod therein.

36. The kit of claim 34, wherein the elongate portion of each of the plurality of connector members has a length different from the length of the elongate portion of another one of each of the plurality of connector members.

37. The kit of claim 34, wherein the elongate portion of each of the plurality of connector members has radius of curvature different from the radius of curvature of the elongate portion of another one of each of the plurality of connector members.

* * * * *